United States Patent [19]

Lassen et al.

[11] Patent Number: 4,673,403
[45] Date of Patent: Jun. 16, 1987

[54] METHOD AND PAD ALLOWING IMPROVED PLACEMENT OF CATAMENIAL DEVICE

[75] Inventors: Frederich O. Lassen, Neenah; Earle H. Sherrod; Ann M. Nichols, both of Appleton; Paul J. Serbiak, Green Bay, all of Wis.

[73] Assignee: Kimberly-Clark Corporation, Neenah, Wis.

[21] Appl. No.: 792,730

[22] Filed: Oct. 30, 1985

[51] Int. Cl.$^4$ .............................................. A61F 13/16
[52] U.S. Cl. ................................. 604/385 R; 604/361
[58] Field of Search .................... 604/385.1, 358, 367, 604/368, 369, 370, 374, 379, 361

[56] References Cited

U.S. PATENT DOCUMENTS

| | | | |
|---|---|---|---|
| 2,067,961 | 1/1937 | Williams | 604/385.1 X |
| 2,092,346 | 9/1937 | Arone | 604/401 |
| 2,331,355 | 10/1943 | Strongson | 604/385 |
| 2,662,527 | 12/1953 | Jacks | 604/385 |
| 3,073,309 | 1/1963 | Mosier . | |
| 3,092,109 | 6/1963 | Mosier . | |
| 3,115,877 | 12/1963 | Harwood | 604/385.1 |
| 3,117,577 | 1/1964 | Mosier | 604/401 |
| 3,121,427 | 2/1968 | Mosier . | |
| 3,146,113 | 8/1964 | Mills . | |
| 3,183,909 | 5/1965 | Roehr | 604/385.1 |
| 3,406,689 | 10/1968 | Hicks et al. | 604/401 |
| 3,528,422 | 9/1970 | Hodas | 604/385.1 |
| 3,983,873 | 10/1976 | Hirschman | 604/385 |
| 4,046,147 | 9/1977 | Berg | 604/385.1 |
| 4,079,739 | 3/1978 | Whitehead | 604/387 |
| 4,184,498 | 1/1980 | Franco | 604/387 |
| 4,340,058 | 7/1982 | Pierce et al. | 604/385 R |
| 4,372,312 | 2/1983 | Fendler . | |
| 4,397,644 | 8/1983 | Mathews et al. | 604/378 |
| 4,405,326 | 9/1983 | Lenaghan | 604/393 |
| 4,433,972 | 2/1984 | Malfitano | 604/385 |

FOREIGN PATENT DOCUMENTS

| | | | |
|---|---|---|---|
| 2420339 | 8/1956 | France . | |
| 754481 | 3/1978 | France . | |
| 2513115 | 3/1983 | France | 604/385.1 |
| 204076 | 4/1939 | Switzerland . | |

Primary Examiner—John D. Yasko
Attorney, Agent, or Firm—P. A. Leipold; D. L. Traut; J. J. Duggan

[57] ABSTRACT

The invention is generally accomplished by providing an incontinent garment or feminine pad having an indicator thereon to aid in proper placement of the pad onto the body of the wearer.

The invention in preferred form provides a sanitary napkin configured for partial labial disposition within the vestibule of the wearer, and for at least partially occluding said vestibule respecting fluid flow therefrom, said napkin comprises a fluid-absorbent body having a posterior region including a raised profile for projection within the vestibule intermediate the labia majora inwardly bounding the same from a position posteriorly remote from the clitoris and extending to the rearwardmost aspect of said vestibule, and anterior region merging with said posterior region and for generally external disposition about the vulvar region over said labia majora and spaced from said clitoris with a visual and/or tactile indicator located in the area of the pad that is to be placed immediately below the vestibule of the wearer.

29 Claims, 23 Drawing Figures 4,673,403

METHOD AND PAD ALLOWING IMPROVED PLACEMENT OF CATAMENIAL DEVICE

TECHNICAL FIELD

The present invention relates generally to the field of devices for absorbing bodily exudate, particularly sanitary napkins for personal feminine care or protection in order to absorb or otherwise contain menstrual fluids or similar exudate, perhaps urine as a consequence of minor incontinence, or the like. The invention more particularly relates to a labial pad offering enhanced fit and comfort through a construction which promotes a self-conforming anatomical cooperation of the pad with the wearer and with providing such a pad with a means of proper placement as the smaller size of such pad requires accurate placement to be most effective.

DESCRIPTION OF THE BACKGROUND ART

There have been a variety of devices or appliances configured for catamenial devices. Generally there have been offered two basic kinds of feminine protection device. These are sanitary napkins or pads that have been developed for external wear, and tampons that have been developed for residence within the vaginal cavity and interruption of menstrual flow therefrom. Each has offered distinct advantages. Hybrid devices attempted to merge the structural features of both within a single type of device have also been proposed.

There has been proposed in the U.S. patent application Ser. No. 707,338 filed Mar. 1, 1985, inventors F. O. Lassen at al., a labial pad that is particularly advantageous in that it is a discreet, comfortable, and highly effective pad. However, while this pad has been particularly successful in functioning as a catamenial device when properly placed, its small size and unique design has made difficult the education of the wearer as to proper placement.

There arises a need for a method of insuring proper placement of an interlabial pad such that it will be properly worn so that it will be effective and reduces leakage. Further, it would be desirable if the pad itself would indicate to the user when leakage was caused by improper placement to eliminate as a potential problem the failure of the pad to function as the perceived cause. Therefore, there is a need for an improvement in formation and use of feminine pads to allow for their proper placement.

DESCRIPTION OF THE INVENTION

An object of this invention to overcome the disadvantages of prior devices for absorption of body exudate.

Another object of the invention is to provide aid in proper placement of devices for absorption of bodily exudate.

An additional object is to provide indication that failure of a catamenial device was caused by improper placement if, indeed, that was the cause.

An additional object of the invention is to increase proper placement of feminine pads.

These and other objects of the invention are generally accomplished by providing an incontinence device, feminine pad or napkin having an indicator thereon to aid in proper placement of the pad such that the indicator is in the area of greatest body exudate flow.

The preferred form of the invention provides a sanitary napkin configured for partial labial disposition within the vestibule of the wearer, and for at least partially occluding said vestibule respecting fluid flow therefrom, said napkin comprises a fluid-absorbent body having a posterior region including a raised profile for projection within the vestibule intermediate the labia majora inwardly bounding the same from a position posteriorly remote from the clitoris and extending to the rearwardmost aspect of said vestibule, and anterior region merging with said posterior region and for generally external disposition about the vulvar region over said labia majora and spaced from said clitoris with a visual and/or tactual indicator located in the area of the pad that is to be placed immediately below the vestibule of the wearer to function as a structured indicator means or positioning means for connoting when the napkin is properly placed to at least partially occlude the vestibule.

DETAILED DESCRIPTION OF THE PREFERRED EMBODIMENTS

The present invention relates, generally, to garments designed to absorb or otherwise contain menstrual fluid or similar exudate, perhaps urine as a consequence of minor incontinence, or the like. The devices with the flow zone indicator of the invention may be incontinence garments for men or women or catamenial devices for women.

The present invention in its preferred form, relates more especially to sanitary napkins shaped or contoured in order to achieve interposition within the vestibule of a wearer for occluding flow of body fluids prior to egress. The placement of such pads as they are smaller than ordinary pads and are shaped for comfortable and effective fit in the vestibule requires proper placement in order to be most effective. Accordingly, the present invention in its preferred form provides for the identification of the target region for proper accurate placement of the pad. The flow zone markings provide structural means to allow for accurate placement of the labial pad below the vaginal opening where it is most effective for most women. However, anatomical differences make the placement for some women to be preferred in a somewhat more forward area. For women with anatomical differences, the wearer can place the target where the most staining occurred on the previous pad and thereby achieve individualized accurate and effective placement. The term "accurate placement" as used herein indicates the placement where a pad will be most effective in receiving and capturing the flow of bodily exudate. In its broader form, the invention allows proper placement of any pad utilized for protection from egress of any bodily fluids. These and other advantages will become apparent from the detailed description of the drawings below. There has been proposed in the copending coassigned patent application entitled LABIAL SANITARY PAD, Ser. No. 707,338 filed Mar. 1, 1985, inventors Lassen et al., an improved labial sanitary napkin. This disclosure is hereby incorporated by reference and is expressly relied upon.

The instant invention will be described with reference to its preferred embodiment, the labial pad of U.S. Ser. No. 707,338 filed Mar. 1, 1985.

Figure 1:
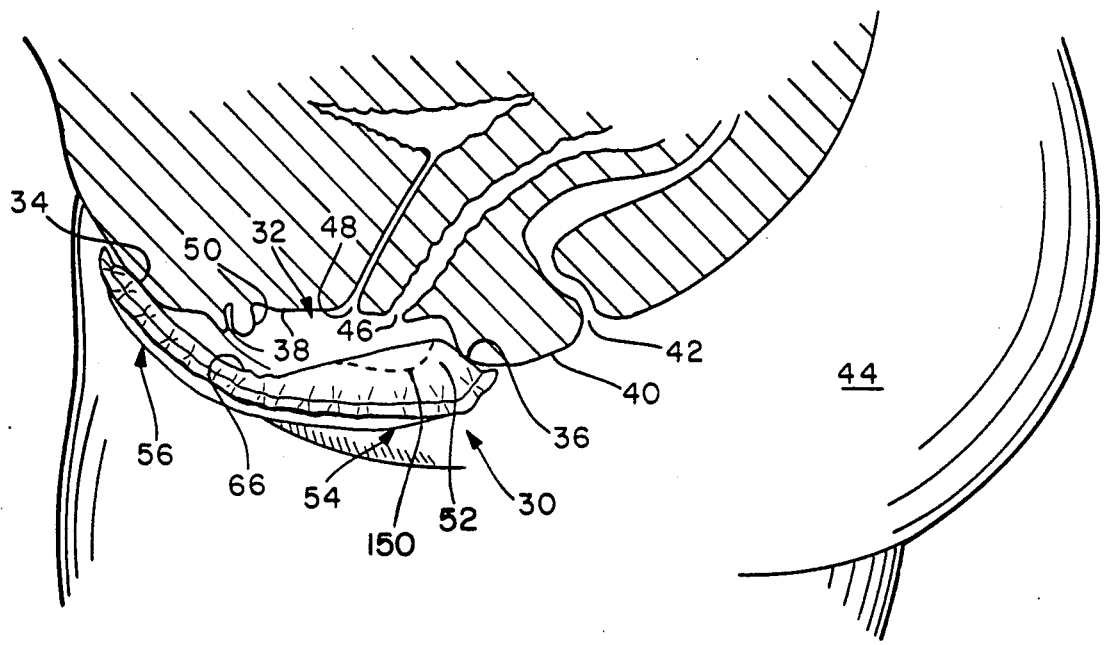
FIG. 1 is a simplified anatomical section illustrating the environment for a labial pad in accordance with the present invention, shown in residence within the vestibule of a wearer.
Figure 2:
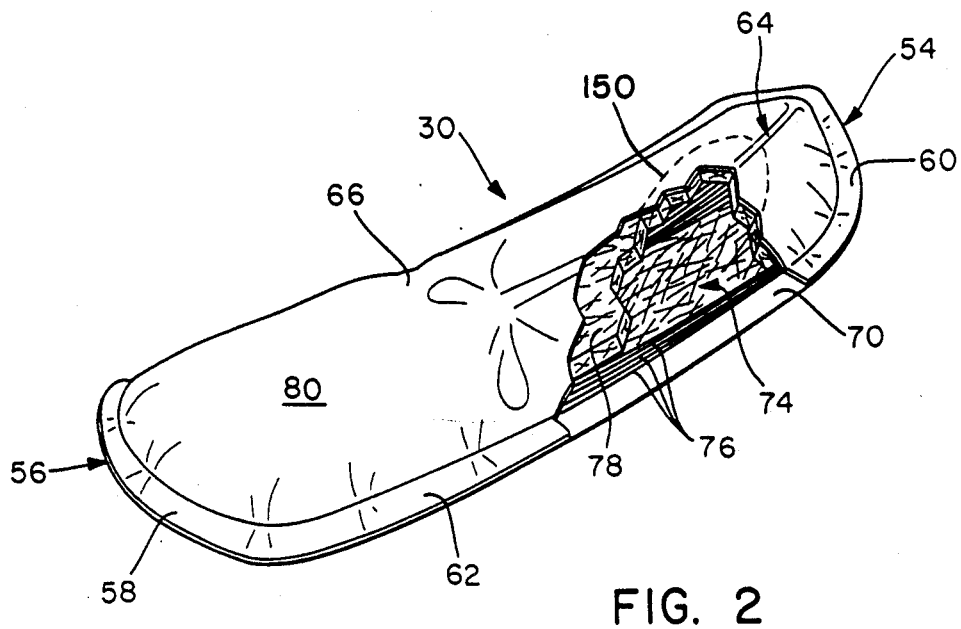
FIG. 2 is an isometric view of a labial pad in accordance with the present invention, with parts broken away to reveal internal components thereof.

Turning to the figures of drawing, in each of which like parts are identified with like reference characters, FIG. 1 illustrates diagrammatically a labial pad in accordance with the present invention designated generally as 30, disposed within the vestibule of a wearer, designated generally as 32. As used herein, the term "labial pad" connotes a sanitary napkin or like article of commerce having a portion specifically configured for disposition between the labia majora, extending into the vestibule, or particularly adapted to achieve that anatomical conformity when put to use. For purposes of the ensuing description, the vestibule is considered to be the region defined within the labia (not specifically shown in the figures herein) beginning at about a point lying caudally from the anterior labial commissure 34, extending rearward to the posterior labial commissure 36 and bounded inwardly by the floor 38. Those skilled in the art fully understand that there is a wide range of variation among women with respect to the relative size and shape of labia majora and labia minora as the same interrelatedly define the contours of the vestibule. For purposes of the present description, however, such differences will not specifically be addressed, it being recognized that in any event the disposition of the labial pad of the present invention into the vestibule will necessitate placement between the labia majora regardless of any such consideration respecting the labia minora. Lying caudally of the vestibule 32 is the perineum 40 which leads to the anus 42 in the region of the buttocks 44. Within the vestibule itself is located the principal urogenital members which, for purposes pertinent here, are constituted of the vaginal orifice 46, the urethral orifice 48, and the clitoris 50. Given the foregoing simplified review of this anatomical region, and to facilitate the pesent description, the vestibule will be considered generally to be the region between the clitoris 50 and posterior labial commissure 36, for convenience sake. For a fuller description of this portion of the female anatomy, however, attention is invited to *Gray's Anatomy*, Clemente 30th Ed. (1985) at 1571–1581.

As can be seen with reference to the anatomical structure depicted in FIG. 1, the labial pad 30 of the present invention is disposed partially within the vestibule 32 for occluding the same respecting fluid flow therefrom. In this regard, the predominant use of the labial pad 30 is for the absorption of menstrual fluid emitted via the vaginal orifice 46; although the labial pad of the pesent invention is equally well adapted to serve as a type of incontinence device for absorption of urine as occurs upon minor, female incontinence. Without particular regard to the type of fluid to be intercepted, the labial pad 30 includes a raised projection or profile identified generally as 52 lying within the posterior region of the pad, denoted generally as 54. The pad further includes a target zone or flow zone 150 enabling the proper placement of the pad. The raised profile 52 is that region of the pad which protrudes within the vestibule and does so intermediate the labia majora inwardly bounding same from a position beginning posteriorly remote (and slightly caudally) from the clitoris 50 and extending to the rearwardmost aspect of the vestibule 32, abutting the posterior labial commissure 36 and generally occluding that region of the vestibule against, e.g., menses. As best viewed in FIG. 1, the projection within the posterior region the pad is most preferably dimensioned or otherwise contoured to avoid contact with the urogenital elements of the wearer's anatomy. In the context of this description, the term "projection" is employed to convey the thought that the pad 30 includes a component, preferably integral therewith or otherwise a part thereof, which "projects" upwardly from the external interface of plane of the pad and the wearer's vulva to reside at least partially within the vestibule (i.e., upwardly from a location between the labia). The "projection" may be entirely coincident with the "profile," although that is not a structural requirement nor are the two terms employed herein necessarily synonymous for purposes of interpretation. Continuing further with this concept, the projection can be visualized to include a "prominence," which connotes the region of the projection which rises to the highest point as measured from the above-mentioned interface or plane. With the foregoing definitional background, the skilled artisan will understand that these terms do not necessarily compel the presence of a free standing structure which is shape sustaining prior to use, in the sense that a clearly defined projection is structurally identifiable prior to disposition within the vestibule to occlude the same. Quite to the contrary, the projection may be fairly ill-defined or unrecognizable prior to use of the pad 30; however, upon proper anatomical cooperation between the pad and the vestibule of the user as occurs upon use, the structural forms or features will take on the definitive shapes shown and described herein. For example, in certain embodiments of the present invention, the labial pad may have an overall shape prior to use visually indistinguishable from a conventional "mini pad," yet when put to use it will adopt the profile described above. Accordingly, those skilled in the art will appreciate that the figures herein and description thereof represent but one visualization of these elements of the invention for the convenience of a complete portrayal.

The pad 30 also includes an anterior region identified generally as 56 which merges with the posterior region 54 generally intermediate the overall length of the pad. The anterior region 56 is configured for external disposition about the forward vulvar region toward the mons pubis, over the labia majora and spaced from the clitoris 50 such that the highly sensitive genital tissue is not in contact with the pad but is, to the distinct contrary, spaced or isolated therefrom. In this manner a line of occlusion is defined in a very general sense within the raised profile of the posterior region of the pad where the same merges into contact within the vestibule of the wearer over the region bounded generally by the posterior labial commissure and the labia majora merging to a point spaced from the clitoris as aforesaid. A general representation of that occluding line within which lies a target zone for receipt of menses or like exudate is depicted generally as the teardrop shaped region best viewed in FIG. 4, the intention there being simply to idealize the representation of that zone. Those skilled in the art will appreciate that the vast anatomical differences to be encountered among the population of users for these types of devices imply widely varying contours for that target zone or line of occlusion; the ability of the instant pad to achieve a self-conforming anatomical cooperation with that wide array of potential anatomical variations being a significant advancement in this art as will be realized further as this description continues.

Figure 3:
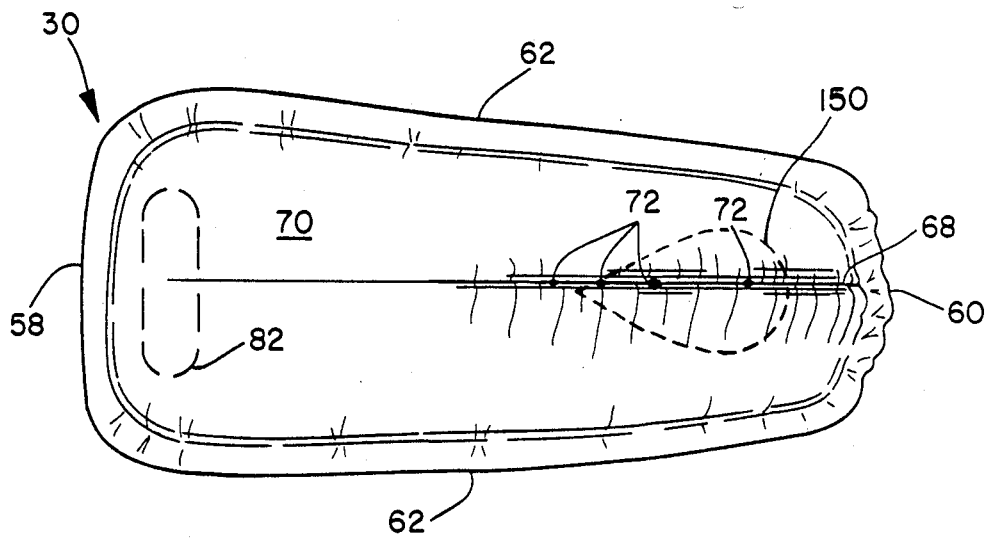
FIG. 3 is bottom plan view of the labial pad shown in FIG. 2 illustrating, in phantom, an optional adhesive element for securing the pad to the undergarment of the wearer.
Figure 4:
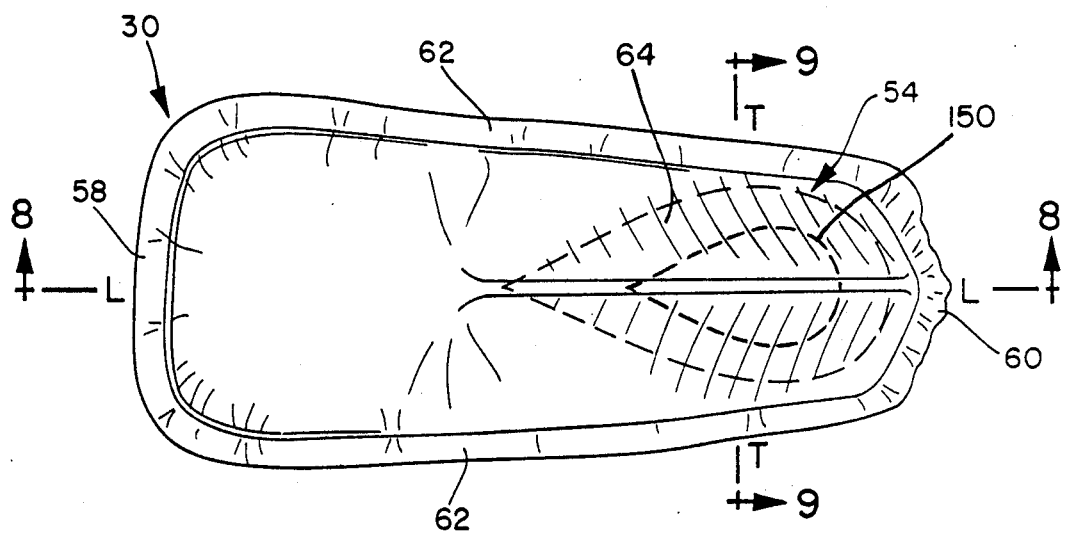
FIG. 4 is a top plan view of the labial pad of the present invention, illustrating in phantom a "target zone" or "flow zone" indicating that portion of the pad destined for interposition within the wearer's vestibule for receipt of fluid.
Figure 5:
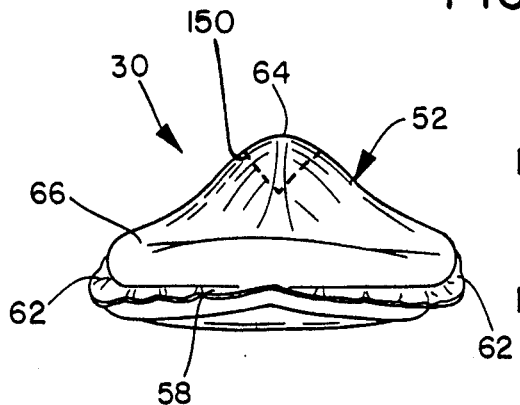
FIG. 5 is an end elevation view from the proximal end of the pad at the present invention.

The pad 30 is shown in its most preferred embodiment to have a generally ovate geometry extending between a proximal end 58 and a distal end 60; e.g., as exemplified in FIGS. 3 and 4, to be slightly wider at the former than the latter. This preferred ovate geometry, including the raised profile of the posterior region 54, is conveniently related to three axes identified in FIGS. 4 and 5 as a principal longitudinal axis "L," a minor transverse axis "T" and a lateral (or height) axis "H." Thus, to complete the overall geometric orientation for purposes of this description, the pad 30 includes longitudinal sides or edges 62 ranging between the ends 58 and 60, these collectively sometimes being referred to herein as the perimetral sides or edges of the pad 30 (i.e., those defining the perimeter). Considering briefly the relative dimensions of a preferred pad, in a functional sense, the same is at least long enough along the longitudinal axis to extend (in use) from the frenulum forward (without significant overlap thereat) to and over the anterior of the vulva; its width as considered across the transverse axis being limited to avoid contact with the legs of the wearer when in use.

Figure 6:
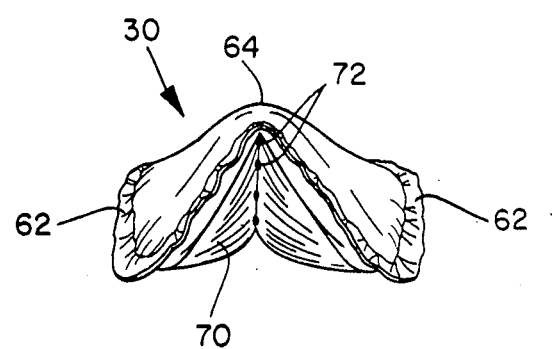
FIG. 6 is an end elevation view from the distal end of the pad of the present invention.
Figure 7:
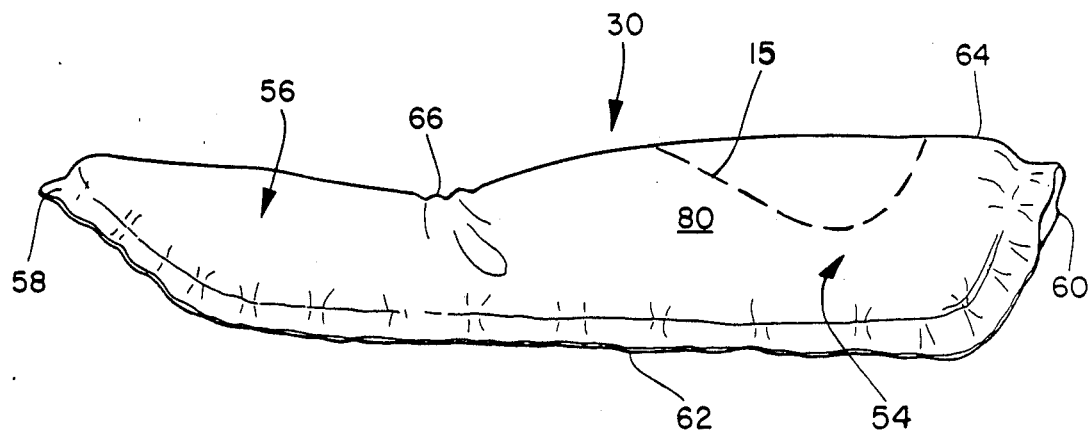
FIG. 7 is a side elevation view of the pad of the present invention.

The raised profile 52 of the pad 30 preferably lies entirely within the posterior region 54 thereof. From a prominence 64 proximate the distal end 60, the profile tapers gently toward the proximal end 58 in the longitudinal direction and also toward the opposed longitudinal sides 62 in the transverse direction, as best viewed, for example, in FIGS. 5–7. The profile continues with a taper or downward slope in the forward direction to a juncture 66 with the anterior region which, in the embodiment illustrated, has a very gradual rise toward the proximal end 58 but of lesser slope than that in the posterior region. Inasmuch as the composiiton of the pad 30 is, overall, relatively compressible with slight resilience, and further insofar as the pad is intended to be generally self-conforming in use, those skilled in the art will appreciate that this structure is flexible and may be imparted with other similar suitable shapes without necessarily departing from the spirit of the present invention. Because of this ability of conformance and ease of flexibility, the raised profile is most preferably impressed in the overall structure by means of a profile precursor established within the pad itself. This may be achieved in one preferred aspect of the invention by providing a longitudinal set to the pad; i.e., a preferential fold or crease along the longitudinal axis as best viewed in FIGS. 3–6, which tends to pitch the pad upwardly along that fold. In this case, a longitudinal pleat 68 is formed within the bottom face or surface 70 of the pad, which, in turn, creates the prominence 64 contributing to the raised profile 52; whether as a strict manufacturing consequence and, hence, as a shape-sustaining structural element prior to use or, alternatively as a zone or line of structural partiality which creates the profile due to conformance in use. In the highly preferred form shown in these figures, the bottom surface 70 is comprised of the conventional baffle member or fluid impervious shield customarily incorporated within a sanitary napkin. Advantageously, therefore, as a polymeric film or nonwoven material bearing a polymeric film, the set or pleat developed upon folding will yield a highly preferential crease line along the longitudinal axis "L." Several options have been devised to complement this longitudinal folding of the pad, or even supplant it, with the objective of establishing a preferential development of a profile precursor. For example, the absorbent body may be slitted along or proximate the longitudinal centerline or axis. The slit may be completely through the absorbent core relative the the "H" axis. Likewise, the slit may be continuous along the core relative to the "L" axis, or discontinuous; i.e., in respect of the latter option, a perforated line contributing to the preferential fold or set. Depending upon the nature and composition of the core, as explained more fully below, the set may be established by an embossment. Other approaches will occur to the skilled artisan for achieving the goal of, ultimately, providing the profile precursor which, in turn, assists in the most advantageous anatomical cooperation between the pad and the wearer.

It is preferred to maintain this profile precursor achieved through the pleat 68, or through whatever other option is elected, in a relatively permanent configuration. The orientation may be conveniently ensured as a somewhat enduring one by means of at least one and preferably several adhesive junctures 72 disposed within the interior apex of the pleat as best viewed, for example, in FIG. 3. Under most circumstances, a single juncture 72 spaced suitably from the distal end 60 will suffice to maintain the profile precursor in an adequate shape to accommodate the anatomical variations to be anticipated amongst most users. Optionally, however, an added measure of adjustability can be included by providing a series of adhesive junctures or bond points such as shown in the figures of drawing, wherein each bond point is selectively interruptible. In that manner, the user may tailor the length and prominence dimensions of the projection 52 by suitably interrupting (i.e., breaking) one or more of those adhesives junctures 72 prior to use. Thus, the range of sizes and geometries achievable by means of the present invention are both extended significantly. Other similar variations are envisioned for providing additional user conveniences in tailoring specific dimensional variations to suit individual preferences. A single line of such selectively interruptible bond points as shown in the figures allows the user to adjust the location of the prominence 64, particularly relative to the longitudinal axis "L." Staggering those bond points in a "W"-like zig-zag pattern permits further adjustability in the height of the prominence. As the skilled artisan will appreciate, these junctures or bond points 72 need not be adhesively formed, but may result from thermal bonding or the like, particularly in those situations where the bottom surface of the pad is composed of a polymeric baffle member. Likewise, a zone of adhesive may optionally replace the discrete junctures should that be a desirable approach. Regardless of the mode of implementation, through, the objective of selectively tailoring the pad dimensions is advantageously provided as a user option.

Figure 8:
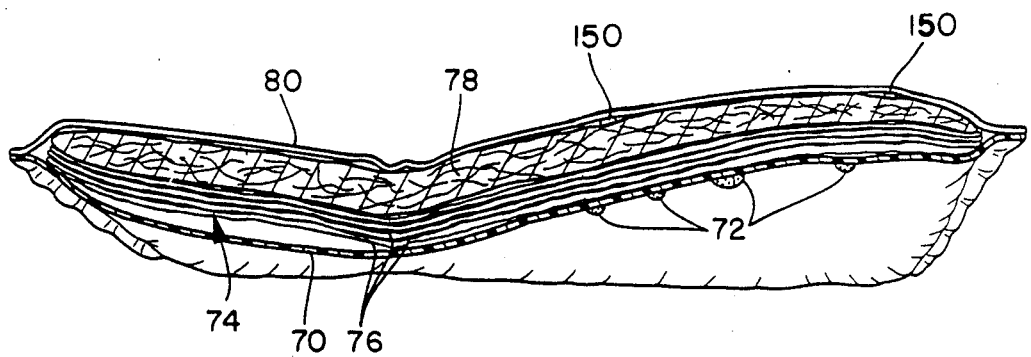
FIG. 8 is a longitudinal sectional view, taken substantially along the line 8—8 of FIG. 4.
Figure 9:
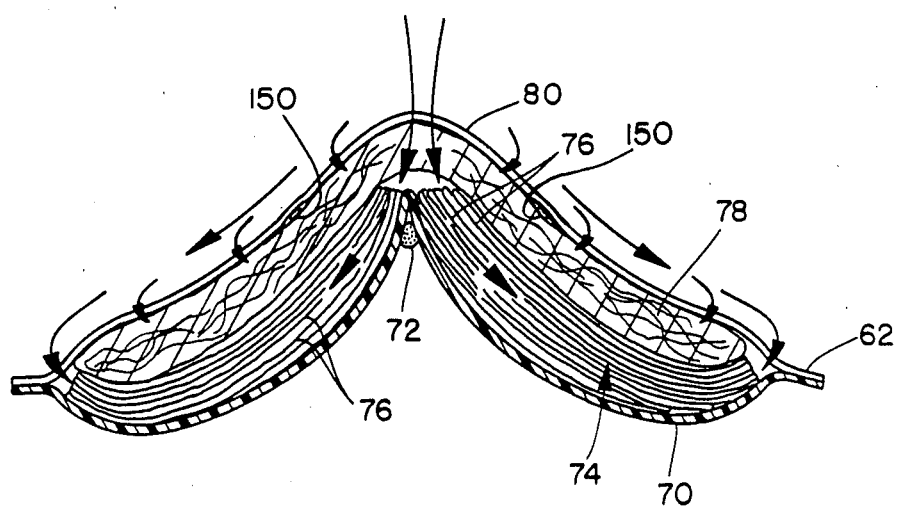
FIG. 9 is a transverse sectional view within the posterior region of the labial pad of the present invention, taken substantially along the line 9—9 of FIG. 4, and further illustrating the flow pattern (both principal and secondary) of body fluids received by the instant pad and distributed thereabout.
Figure 10:
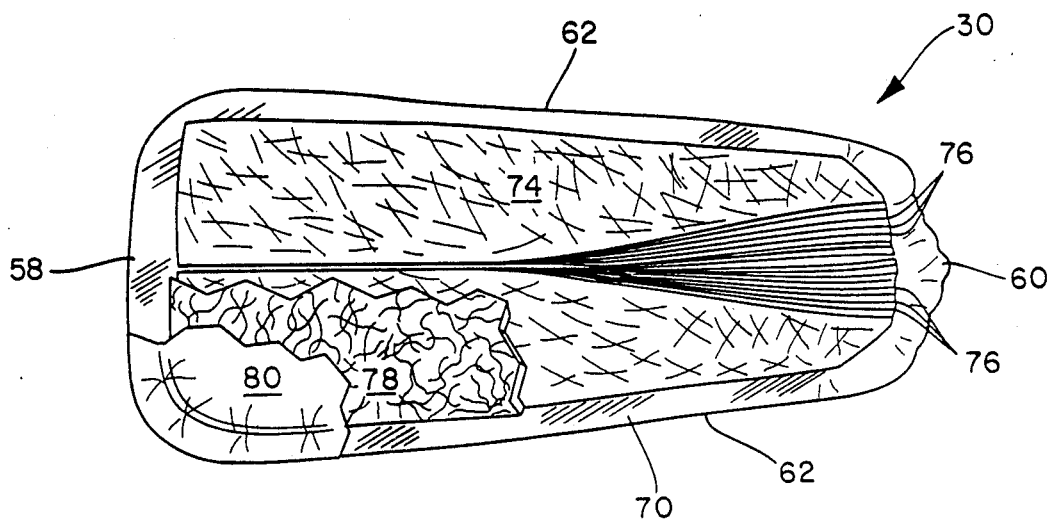
FIG. 10 is a top plan view of a pad in accordance with the present invention, similar to that of FIG. 4, but with parts broken away to illustrate the peferred orientation of microfibrous webs within the absorbent body thereof.

The absorbent capacity of the pad 30 of the present invention is provided by a fluid retentive core or absorbent body identified generally as 74. In general, the absorbent body 74 may be comprised of any conventional absorbent composition including, for example, cellulosic batt(s). However, the highly preferred structure for the absorbent body 74 illustrated in the figures of drawing is in the nature of a microfibrous absorbent. More preferably yet, the absorbent body 74 is comprised of a plurality of individual microfibrous webs 76 disposed in generally face-to-face engagement within longitudinal zones lying along the longitudinal centerline "L" of the pad 30. Most preferably the microfibrous batts 76 are located in a highly efficient orientation, with the batts being placed edgewise within the posterior region immediately across the longitudinal axis (and thus within the target zone) while lying facewise in the anterior region and along the perimetral edges of the posterior region. This relationship is best viewed with reference to FIGS. 8-10, showing the manner in which the composite of microfibrous batts twists along the longitudinal axis to achieve that highly preferred orientation. This presents the most effective angle of incidence for capillarity within the target zone to achieve rapid wicking distribution of menses of the like with correlative fluid distribution in the X-Y direction once received within the absorbent core, a feature considered in greater detail below. The microfibrous webs may be replaced by other wicking or absorbent materials adapted for retention of fluid, and preferably a batt or member having absorbent characteristics approaching the capillarity of microfibers. A suitable alternative in many cases is a densified cellulosic fiber web with a density in the range of from about 0.15 to about 0.30 gm/cc. and preferably about 0.2 gm/cc. Regardless of the absorbent core adopted, whether one of the foregoing or an equivalent, a transfer layer 78 overlies the core to assist in this preferred fluid distribution, as also noted below.

Figure 14:
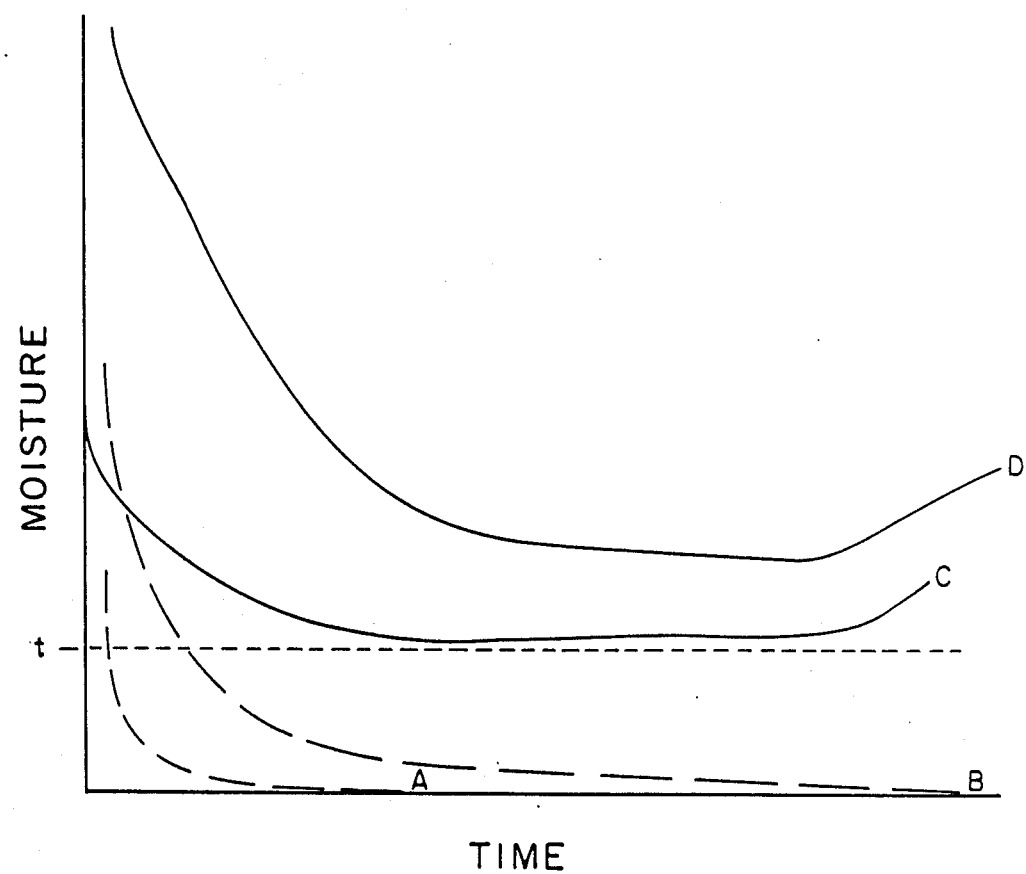
FIG. 14 is a simplified graph showing a comparison of the moisture characteristics of various cover materials for a labial pad of the present invention as contrasted with conventional cover materials for a sanitary napkin.

Completing the overall structure of the pad 30 is a cover member 80 which optimally possesses certain characteristics particularly selected on account of the labial disposition of the pad relative to the wearer. The conventional wisdom respecting cover materials for sanitary napkins has been pointed toward materials and/or structural orientations which yield two specifically desirable attributes. On the one hand, rapid Z directional transmission of fluid through the cover and away from the wearer's body has been of paramount concern to those working in this art over the years. Second, and closely related, is the desire to provide a dry cover for that interfacial member which is in proximate engagement with the wearer's body. For both physical and psychological reasons, it has been quite important for conventional sanitary napkins to have a dry, nonsmearing interface achieved by optimizing those two characteristics. However, that approach is deemed generally antithetical to the labial pad of the present invention, inasmuch as the same must function within the more hydrous and sensitive tissues of the wearer's vestibule. More specifically, the labia majora and labia minora which bound the gross anatomy of the vestibule include delicate tissues and membrances which are physiologically hydrous in the sense that the same maintain an ideal level of moisture within the urogenital region. Disposing a conventional cover material within that environment, designed to wick rapidly in a Z direction, would contribute to a drying of that sensitive tissue. That would be a most unwelcomed result inasmuch as chafing or other irritability of these delicate tissues would be quite uncomfortable for the wearer. However, it has been determined in accordance with the present invention that the use of a physiologically hydrous cover 80 overcomes those impediments and yields a highly advantageous pad construction. As used herein, that term "physiologically hydrous" is meant to connote a cover material which maintains a suitably moist interface between the tissues of the vestibule and the pad 30 when disposed in that vestibular environment; one that is benign respecting the requirements of comfort associated with the interposition of fabric or fabric-like structures within the moist tissue environment of the vestibule, keeping in mind as well the self-evident factor that the pad is receiving body fluids migrating through the vestibule and must conduct the same to the absorbent core. Thus, while not "hydrous" in the classic sense prior to use (inasmuch as the cover will be dry at that time) the cover maintains (or at least does not interfere with the maintenance of) the proper moisture level or balance required within the vestibule. For example, in considering this feature of physiologically hydrous covers, and with specific reference to FIG. 14, there is shown the response of four different types of cover materials identified A-D correlated with comparable transfer layers. The graph represents the moisture level responses for each of the four materials sampled relative to the time for wicking during normal menstrual flow. Further included is a horizontal indication of a threshold moisture level identified "t," above which optimal results obtain. The curves which are represented in FIG. 14 are generated very simply upon time measurement of the fluid level characteristics of the cover member of a sanitary napkin when associated with the remaining components constituting that structure. That is, for purposes of establishing a quantitative measure to isolate nonacceptable cover candidates from those which meet the requirements of a physiologically hydrous cover in accordance with the present invention, the test is conducted on a cover member when structurally associated as a component of a sanitary napkin. Either a finished sanitary napkin may be used or one constructed simply for testing since a particular cover may be susceptible to wicking variation as a function of the wicking characteristics of an associated transfer layer and the rewetting characteristics of a fluid retentive core. In an effort to establish such a quantitative measure with an eye toward discriminating between acceptable and nonacceptable covers, the following test has been adopted.

A sanitary napkin bearing a cover to be screened is wetted with a measured quantity of water. For purposes of the present test, a discrete spot of ten millileters of water is deposited centrally of the pad to be examined. That moistened pad is placed on a partially filled resilient water bottle (e.g., a conventional household hot water bottle) which is supported upon the top plate of a laboratory jack. Disposed above the jack is a stationary plate against which the pad, borne upon the water bottle, may be urged. Prior to that, however, a moisture probe is located intermediate the wetter portion of the test specimen and the stationary plate. The test is conducted utilizing a commercially available moisture probe marketed by the "Greenthumb Products Company" of Apopka, Fla., U.S.A., intended by the manufacturer to be a houseplant moisture tester. Since the test adopted here is of the "go," "no-go" variety, any probe or other like instrument capable of developing a signal in response to the presence of moisture is equally well adaptable for a similar test, particularly inasmuch as the data of interest are advantageously normalized to the condition of the vestibule, eliminating the need for strict quantitative measurement. The test apparatus couples the probe to a meter with a graduated scale, the precise graduations being of less interest here since relative time/moisture measurements are of concern. With the probe in place, the laboratory jack is raised to establish a pressure of 0.5 psi, conveniently measured through the displacement of water from the resilient water bottle supporting the test specimen. A timer is started when that pressure reading is attained and the gauge readings are recored at 30 seconds, 60 seconds, 120 seconds, 240 seconds, 300 seconds, 600 seconds and 900 seconds. Those readings are plotted on a relative moisture scale as represented in FIG. 14 against the benchmark or threshold level "t" representing the moisture level below which a statistically significant sample of users would find the cover material to be objectionable due to an inability to maintain the necessary physiologically hydrous interface between the prominence of the pad and the vestibule within which it is located during use. Other tests may be adapted to this same end, the foregoing being deemed representative of the preferred approach to be taken in order to characterize suitable materials with these thoughts in mind.

The covers identified as A and B in FIG. 14 are based upon the materials disclosed and claimed in U.S. Pat. No. 4,397,644. In both cases, while that cover material is admirably suited for a conventional sanitary napkin, it is seen that the rapid wicking and very dry characteristics typical of those species are quite ill-suited for use as a labial pad. To the contrary, the compositions identified as C and D respond quite differently. Upon initial flow there will be a wicking of fluid into the absorbent core and away from the interface. Over a course of time, that interface will attain a generally steady state flow, passing fluid through the cover at approximately the same rate as it is received. Then, after loading of the absorbent core has begun, and the gradient in moisture is reduced across the cover, even a slight increase in the moisture level (i.e., a decrease in flow gradient) will be seen to occur; although the slight reversal in flow is not a requirement for the cover of the present invention (in this case, it is simply a consequence of adopting specific materials within the most preferred of embodiments as related below). Irrespective of that facet, the covers exhibit the type of physiologically hydrous characteristics deemed most preferred in accordance with the present invention. With the appreciation for the decided advantage provided by a physiologically hydrous cover for pad 30, those skilled in the art will further appreciate the fact that such a characteristic is required principally within the target zone, or that region of the pad disposed within the vestibule. As a matter of manufacturing convenience, this is assured by fabricating the pad with a top cover of appropriate material whereby the entire top surface exhibits this feature. However, that is not an absolute requirement. For example, the physiologically hydrous characteristic may be imparted to the pad by means of coatings or the like applied to the cover (externally or integrally), in which case the same may be confined to the region of the target zone only; i.e., the profile which is intended for interfacial contact with the moist tissue of the vestibule. Other such variations to achieve a zoned distribution of cover properties along these lines will occur to those skilled in the art and, guided by the principles set forth herein, included within the scope of the present invention.

The highly preferred construction outlined above yields a remarkable effective sanitary pad. Fluid is intercepted within the raised profile, and preferably within the target zone identified generally in FIG. 4, after it has been emitted from the vaginal orifice. Prior to a time when this fluid has an opportunity to migrate through the folds of the labia, either forward or rearward as is the case with conventional sanitary napkins, the fluid is caused to contact the profile and be distributed for absorption within the core of the pad. As best viewed in FIG. 9, principal fluid flow is through the physiologically hydrous cover and transfer layer to the oriented microfibrous batts within that region. It is also highly noteworthy to observe a secondary path which is provided during times when increased flow cannot otherwise be accommodated reasonably by the central structure of the pad 30. In this case, fluid may migrate at least in part across the cover (as opposed and/or in addition to through the cover) as shown by the representative arrows in FIG. 9 toward the perimetral sides or edges of the pad. At that juncture, the orientation of the microfibrous batts is again made in the most receptive position relative to flow; whereby that fluid incapable of initial accommodation in the Z direction through the cover and into the absorbent batt is wicked from the edges thereof. Accordingly, a sanitary napkin of materially enhanced absorptive capabilities and collateral reliability in use is provided.

The ability of the labial pad 30 of the present invention to conform anatomically to the wearer's vulva and vestibule area is quite remarkable. Specifically, when disposed initially within the labia majora, the pad 30 of the present invention is self-positioning to a high degree. When the device is properly located by the user, with the prominence 64 disposed in generally abutting engagement with the rearwardmost aspect of the vestibule proximate the anterior labial commissure, a rear line of occlusion is formed thereat. While technically not a true fluid seal, by virtue of the compositional nature of the article, the occluding capabilities as regards the prevention of fluid flow from the rearward area of the vestibule is highly efficient. The normal motion of the user (e.g., walking) tends to reinforce the sealing or occluding effect of the raised region within its zone of engagement with the rearwardmost aspect of the vestibule, thus "sealing" that area. The natural resiliency of the labia tends to compress the body of the pad 30 within the posterior region, with the labia majora lying generally outward of the teardrop-shaped target zone shown in FIG. 4. This slight inward urging or compression provides the line of occlusion within that region. Thus, and as a general consequence of the preferred set imparted to the pad as described above, a highly conforming anatomical fit is achieved which, because that fit relies in part upon the anatomy of the user, is generally self-adjusting. By virtue of the great efficiencies of the oriented microfibrous absorbent webs, providing rapid fluid transfer, that line of sealing or occlusion is generally more than adequate to prevent seepage of fluid outside the zone lying within the vestibule itself. As noted previously, there may be exceptional circumstances during which short duration but heavy flow may not be fully accommodated; however, under those circumstances, the secondary flow path noted with reference to FIG. 9 sufficiently accommodates that eventuality. Regardless of such considerations, the anterior region of the pad 30 lying forwardly of the portion disposed within the vestibule curves gently to conform to the external portion of the vulva of the user as best visualized with reference to FIG. 1. This leaves the clitoris (as well as the other urogenital members) spaced from the pad, unlike many prior art labial constructions, thus guarding against the irritating and perhaps painfully irritating chafing effects which contact can occasion.

The self-conforming characteristics of the labial pad of the present invention render unnecessary a requirement for independent attaching means for the pad. The slight biasing force provided by the wearer's undergarments will establish a sufficient upwardly directed force to maintain the labial pad in the desired position illustrated generally in FIG. 1. However, there may be situations where it is desirable to provide some ancillary attaching means. Accordingly, there is optionally provided a discrete adhesive member identified (in phantom) as 82 in FIG. 3, for securing the pad 30 to the undergarments of a wearer. This adhesive 82 is most preferably a conventional pressure sensitive adhesive bearing a release paper which may be removed to expose the adhesive for purposes of attachment to the undergarment. In this manner, the wearer may exercise the option of attaching the pad or not as a matter of individual preference. It is noteworthy that even in those instances where the option to secure the pad 30 to the undergarment is elected, a comparatively small singular or discrete location or zone for adhesive is most preferably provided as opposed to more conventional longitudinal, multiple strips or the like. Ideally, attachment directly to the undergarment or body is not required, recognizing that such attachment may under some circumstances override the more preferred direct association of the pad solely with the wearer's body; the wearer then facing the possibility that movement of the undergarment relative to the vulva will translate into some motion within the pad itself. Isolating that movement from a single point located near the proximal end of the pad, about which it may pivot, tends to minimize the tendencies toward moving the raised profile of the posterior region of the pad out of its occluding engagement within the vestibule. In this sense, it has been determined that there is a position of relatively neutral action within an undergarment forward of the mons pubis along a type of neutral axis with regard to the legs when the same undergo a walking motion. This neutral point, or so-called point of "stasis," is most preferably the point of cooperative attachment for the adhesive 82. The neutral point is most easily found by considering the pelvic dynamics of a wide range of individuals undergoing walking motion. Such studies reflect the fact that there is a line of neutral motion extending between the legs from a point beginning at about the public symphysis and extending directly to the coccyx. This is in most individuals a line of zero motion across what would generally be deemed the median sagittal plane. The optimal point on that plane, for purposes pertinent to the present discussion regarding attachment of the pad 30, is one which is approximately at the public symphysis. Accordingly, striving for a point of attachment of the pad by means of a single discrete adhesive spot (or limited multiple spots) at or about the public symphysis along the aforementioned line of zero motion is deemed most preferred; although it will normally be found acceptable to have attached the pad at a point lying on or as near as possible to that imaginary line. This approach provides a generally acceptable compromise for those who wish the security of attachment of the pad 30 to the undergarment while that point of attachment is selected as the least influential relative to the potential contribution to rubbing or chafing occasioned by relative motion between the undergarment (and attached pad) and the wearer's vulva.

The preferred labial pad for use of the present invention is highly commendable for its ease of manufacture both in terms of methodology and selection of materials. As a capsulized summary, the pad 30 utilizes a conventional spunbonded nonwoven bearing a suitable polymeric film as a baffle member corresponding to the bottom surface or face 70. Exemplary of such a baffle is a conventional 0.4 oz. per square yard spunbond web with a 0.75 mil (0.00075 in.) film of an ethylene methyl acrylate, preferably with the EMA side toward the body of the absorbent material. To that baffle member is secured the absorbent body, preferably in the form of two opposed stacks of microfibrous webs 76. Most preferably, the microfibrous webs are surfactant treated polypropylene microfibrous webs having a basis weight of 90 grams per square meter. In order to achieve the optimal orientation wherein the plurality of microfibrous webs are disposed edgewise within the target zone and facewise longitudinally outside that region, two alternate approaches are envisioned. In one instance, two individual stacks of microfibrous webs are disposed in side-by-side relationship along the longitudinal axis "L." Alternatively, a single stack may be disposed upon the baffle member and suitably slitted, at least within the posterior region of the pad and optionally entirely along the length thereof to yield the preferred orientation. When this latter approach is adopted, the fabricator has yet the additional option of slitting some, but not all, of those webs to leave one or more in tact at the interface with the shield or baffle 70. The microfibrous absorbent components are overlaid with a transfer layer 78 preferably comprised of a fibrous blend of polyester, rayon, and a polymeric fiber such as that marketed by C. Itoh & Co. under the tradename "CHISSO". A highly preferred composition is comprised of 60% polyester fibers with a length of approximately ¼" (3 dpf), approximately 20% straight rayon with a fiber length of approximately ⅜" (1.5 dpf) and the balance CHISSO with a fiber length also about ⅜" (3 dpf). Other compositions will occur to those of ordinary skill in the art and may be substituted with due consideration for the functional requirements of a transfer layer in terms of a rather rapid wicking of fluid in the Z direction. That transfer layer also beneficially contributes to a rather "springy" characteristic of the top elements of the pad in order to mold to the wearer's body while providing a soft interface; thus the degree of loft being a salient consideratio. Likewise, while principally concerned about efficient Z directional wicking from the cover to the absorbent batt materials, the transfer layer also functions during short duration high flow conditions to distribute fluid in a more transverse direction as need be as may be envisioned with reference to FIG. 9. The transfer layer is overlayed with the preferred physiologically hydrous cover which, as noted above, is selected to maintain a suitably benign physiologically hydrous interface within the environment of the wearer's vestibule. A highly preferred cover is one made from a spunlaced polyester such as that sold under the tradename "SONTARA" by E. I. DuPont Company. Most preferably, a "SONTARA" cover comprised entirely of polyester fiber having a basis weight of about 34 grams per square meter is utilized for this purpose, although suitable equivalents can be adopted provided the same meet the functional requirements aforementioned (e.g., in some instances, even a rayon cover may find good functional utility in this context, as can diverse polymeric materials bearing suitable coatings). The cover is preferably secured to the shield or baffle about the perimetral edges as envisioned best with reference to, e.g., FIGS. 3 and 4, via thermal or adhesive bonding. This yields a border about the perimeter which can vary in width depending upon the fabricator's desires. A pertinent consideration for the border dimension is best considered with reference to the depiction of flow in FIG. 9 which illustrates the alternate flow path provided across the surface of the cover when, e.g., menses may not be accommodated entirely in the Z direction through the cover and into the microfibrous batts. Inasmuch as neither the cover nor the baffle, 80 and 70 respectively, is fluid absorbent under the preferred conditions specified hereinabove, migration of fluid across the cover as shown in FIG. 9 to the perimetral edges will then permit the same to be wicked within the microfibrous batts disposed proximate that juncture. Providing a judiciously sized border will facilitate the ability of fluid to achieve this secondary flow to the absorbent components inasmuch as a border too narrow perhaps will not permit sufficient initial residence time about the edge region for wicking to occur and thereby run off whereas as too wide a border may allow runoff inasmuch as the fluid escapes the region where wicking can occur before that occurrence. A border on the order of about ¼" will under most circumstances be deemed suitable with these thoughts in mind; although, depending upon choice of materials and the like the skilled artisan may need to make specific adjustments which, guided the foregoing principles, are deemed well within the ken of those workers in the field.

Figure 11:
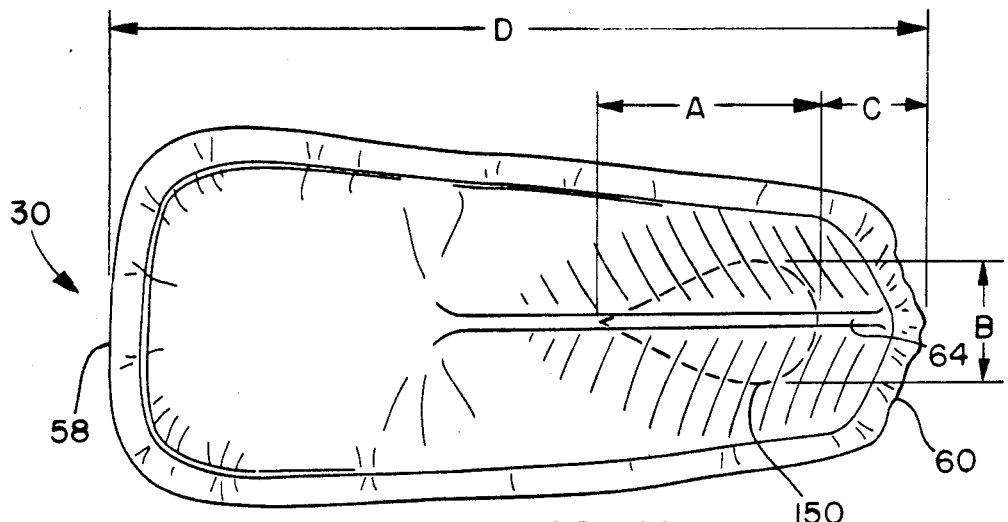
FIG. 11 illustrates a pad of the invention with the area for the flow zone indicated.
Figure 12:
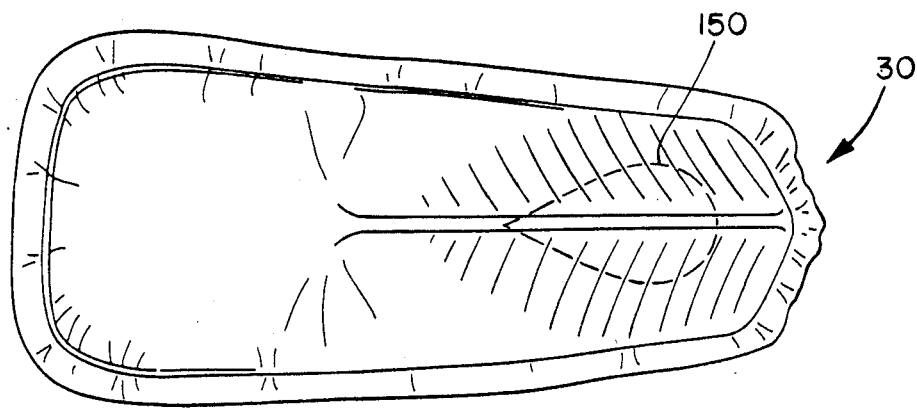
FIG. 12 is a top view of the pad of the invention with the flow zone indicated.
Figure 13A:
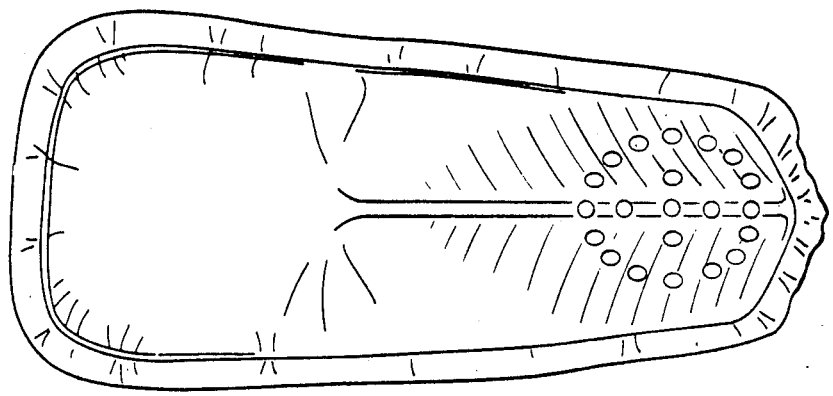
FIGS. 13a through FIG. 13j are top views of pads of the invention with various flow zone markings indicated.
Figure 13B:
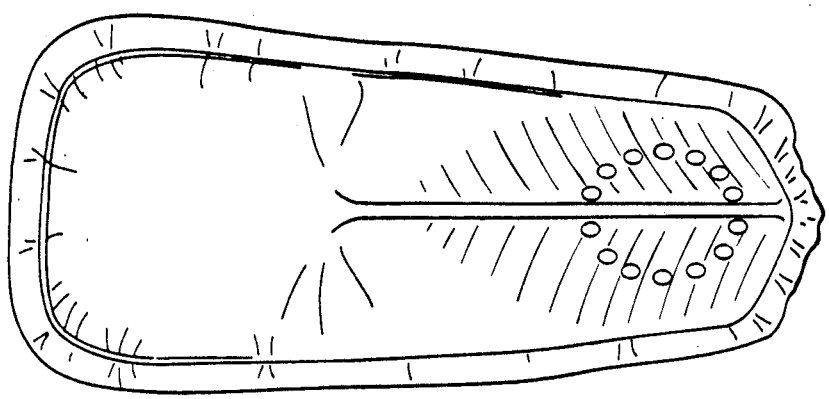
Figure 13C:
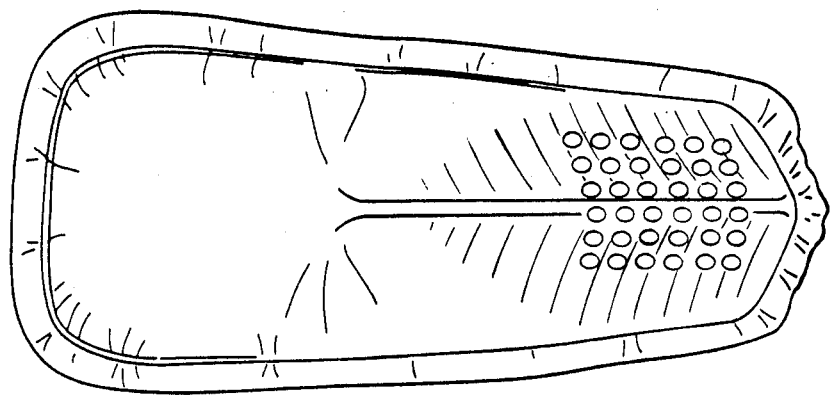
Figure 13D:
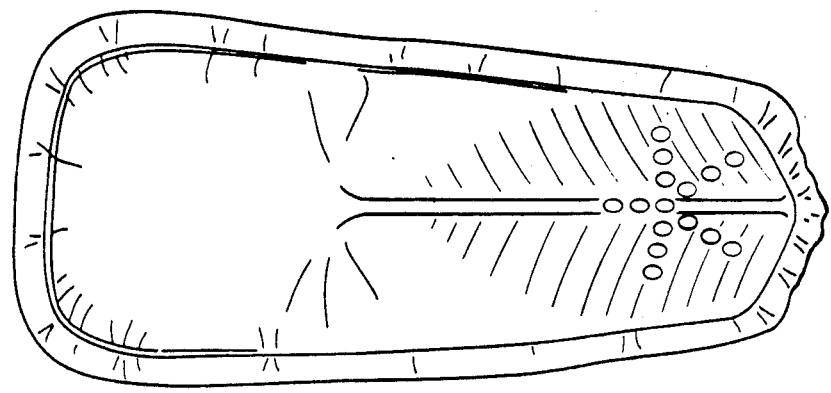
Figure 13E:
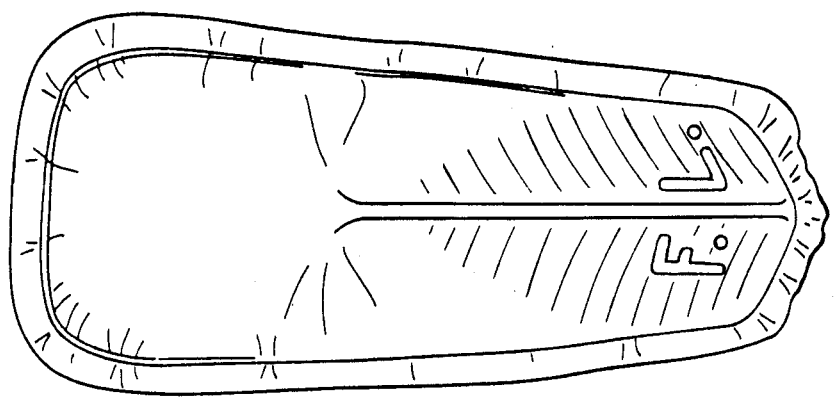
Figure 13F:
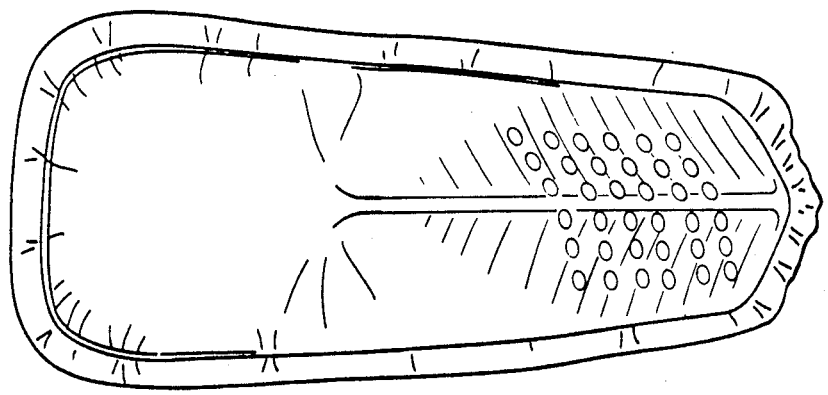
Figure 13G:
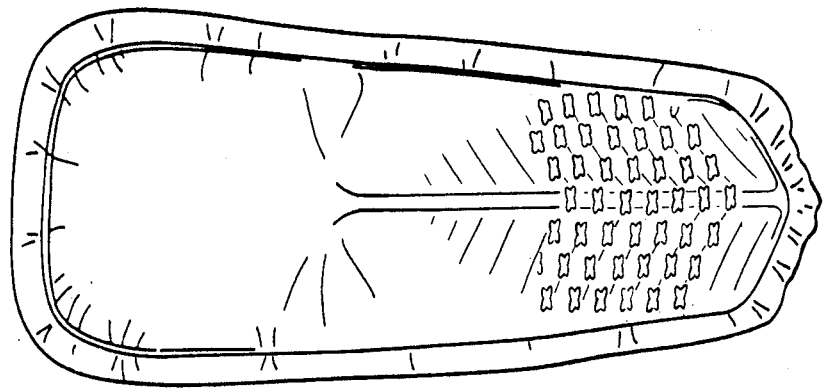
Figure 13H:
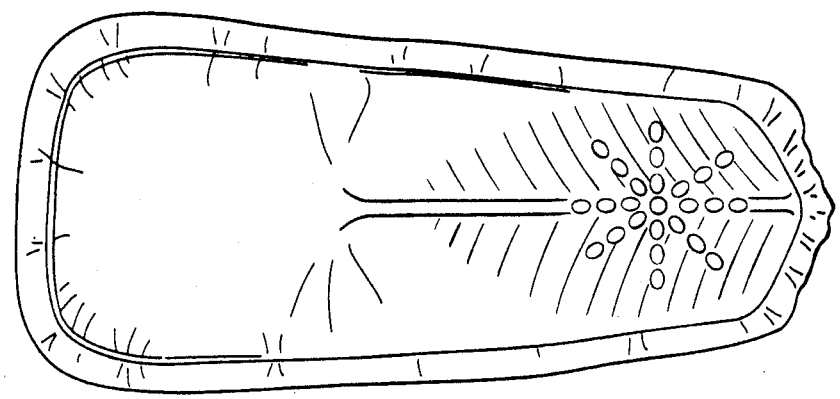
Figure 13I:
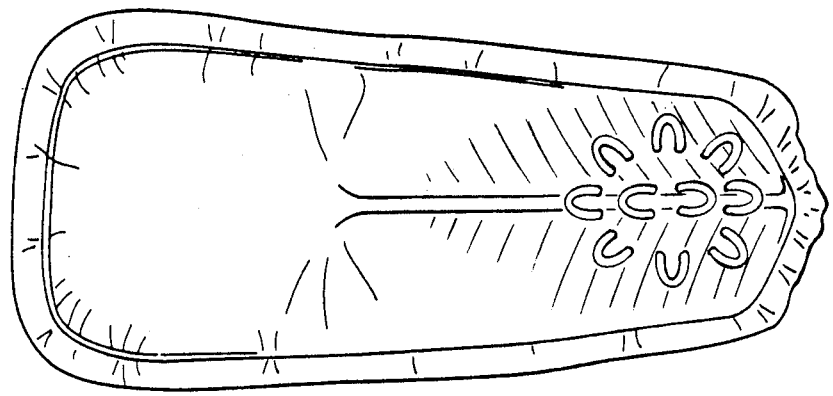
Figure 13J:
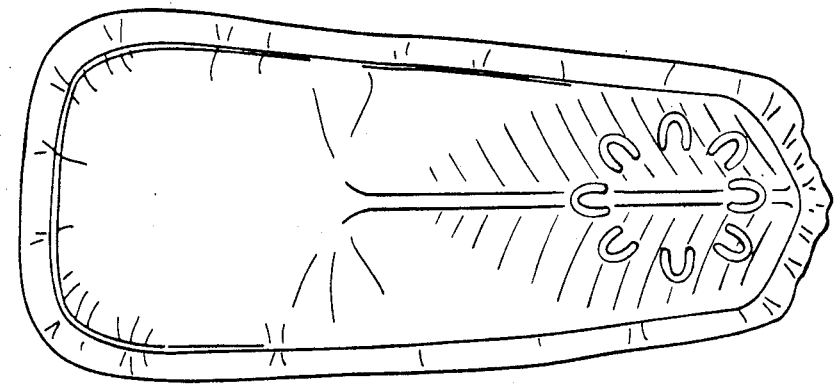

As illustrated in FIG. 11, the target area 150 of the pad 30 is placed below the vaginal orifice for best pad placement and forms a relatively small portion of the overall pad. Generally, the pad's overall length, indicated as "D", will be about 5 to 6 inches. The preferred length is about 5½ inches. The width "B" of the target area 150 is generally about 8% to about 20% of the pad length or between about ½ and 1 inch wide, the preferred width being about 12% to about 15% of the pad length or about ¾ inch wide in the "B" dimension. The "C" dimension where the target area begins from the posterior region is about 8% to about 15% of the pad length or about ½ to about ¾ inch from the posterior end of the pad 60. The target area 150 has an "A" length of generally between about 20% and about 40% or about 1¼ and 2¼ inches. Target area length is generally dependent on overall pad length. The preferred length is about 27% to about 37% or about 1½ to 2 inches in the "A" dimension of FIG. 11 for accurate placement by the typical user. The width of the target area 150 in the "B" dimension is between about ½ inch and 1 inch. The preferred width is about ¾ inch for accurate placement for the typical user.

The means of indicating the target area 150 may be in accordance with the invention any suitable indicator that is not uncomfortable to the user. Typical of such means are a colorant layer on the cover of the pad, a colorant layer below the semitransparent cover of a pad on the absorbent, positioning of a removable indicator on the pad perforation of the cover, or embossing. Further, a combination of methods could be utilized. A preferred method has been found to be placing a colorant layer on the interior of the bodyside cover to provide a visible indicator. A particularly desirable indicator has been found to be a blue indicator of a generally tear-drop shape that both is attractive and provides a pointer toward the front of the pad while also indicating the proper placement with the indicator toward the posterior and generally between the labia majora at the vaginal orifice. The printing on the interior of the cover is preferred as it is visible but does not come directly in contact with the body as some wearers might find this uncomfortable. An alternate means of indicating the target 150 would be embossing a pattern in the target area. Embossing allows placing by feel alone but does not provide the pad with projections that might be uncomfortable to the wearer. This has the advantage that it would allow placement by feel alone. Further, it is possible that a combination of embossing and printing could be utilized, although there would be an increase of cost in the additional processing necessary. The indication of target area is also desirable as the user is able to determine if the device was properly placed for her body by study of the staining after use.

FIGS. 13a through 13j indicate a variety of patterns on pads of the invention that could be utilized for indicating the target area. The embodiments of FIGS. 13a through 13j are each suitable for either embossing or printing. As is apparent from a review of these target area indicators, the target area may be indicated in a variety of decorative ways. Further, it is possible that the target indication also could be combined with improvements in flow caused by impression or perforation of the cover stock in the target area. However, the bodyside cover material being selected to be physiologically hydrous in its preferred form generally does not need to be provided with flow-increasing properties.

Any suitable ink may be utilized for marking of the pad to provide visible indicator. Suitable inks will be nonirritating to the wearer and permanent so as not to stain the wearer. A particularly preferred ink is FLEXO 910 light blue ink No. 85NK395 from Fremond Inks. The ink may be printed by any suitable methods such as printing, silkscreen, or spraying.

While the invention has been discussed with particular reference to the preferred labial pad, it is also desirable for other labial pads as well as larger catamenial pad devices or incontinence protection devices. There is a common need for all such devices to be properly placed. Therefore, the placement of a target indicator by a safe, effective method would be desirable. The method of applying the indicator by ink or embossing would be the same whether the above-described labial pad was utilized or a larger catamenial pad or an incontinence pad. The scope of the invention is only intended to be limited by the scope of the claims attached hereto.

We claim:

1. A device for absorption of body exudate comprising an absorbent pad, a liquid permeable body side member, a liquid impermeable backing member and said absorbent therebetween wherein there is provided on the body side of said device a flow zone indicator means for connoting accurate placement of said pad onto the wearer's body in the region where greatest exudate flow will contact the flow zone indicator such that the wearer of said pad is able to adjust placement of said pad to locate it in the area of greatest exudate flow.

2. The device of claim 1 wherein said pad, a feminine napkin, is configured for at least partial labial disposition.

3. The device of claim 1 wherein said indicator comprises ink printed on the underside of a bodyside cover material of the pad.

4. The device of claim 1 wherein said indicator is disposed in the region of the pad to be placed to occlude the vaginal opening.

5. The device of claim 1 wherein said indicator means comprises embossing as the indicator.

6. The device of claim 1 wherein said indicator is an area both embossed and colored.

7. The device of claim 1 wherein said indicator is colorant printed on the absorbent of the pad below a semitransparent cover.

8. The device of claim 1 wherein said indicator is an apertured area of the bodyside cover of said pad.

9. The device of claim 1 comprising an incontinence pad.

10. An anatomically, generally self-conforming sanitary napkin configured for partial labial disposition within the vestibule of a wearer and for at least partially occluding said vestibule respecting fluid flow therefrom, said napkin comprising a fluid absorbent body having a posterior region included a raised profile for projection within said vestibule intermediate the labia majora inwardly bounding same from a position posteriorly remote from the clitoris and extending to the rearwardmost aspect of said vestibule, and an anterior region merging with said posterior region for a generally external disposition about the vulvar region over said labia majora and spaced from said clitoris wherein said pad is provided on the body side with an indicator means for connoting when said napkin is in a position at least partially occluding said vestibule.

11. The sanitary napkin of claim 10, wherein said fluid absorbent body is comprised of a top, bodyside surface, a bottom, garment-contacting surface, and perimetral sides, said raised profile extending from said top surface within said posterior region.

12. The sanitary napkin of claim 10, wherein said raised profile is impressed within said fluid-absorbent body, having a generally shape-sustainable precursor configuration for projection within said vestibule.

13. The sanitary napkin of claim 12, wherein said fluid absorbent body includes a generally longitudinal pleat extending from the posterior end of said napkin and centrally-disposed relative to the opposed sides thereof for establishing a profile precursor having a generally transverse curvature respecting said longitudinal pleat.

14. The sanitary napkin of claim 13, wherein said pleat includes at least one bond juncture within the interior vertex region of said bottom surface for maintaining said profile precursor.

15. The napkin of claim 10 wherein said indicator means comprises a color indicator contrasting with the remainder of the bodyside surface of said napkin.

16. The napkin of claim 10 wherein said indicator means comprises an embossed area.

17. The napkin of claim 10 wherein said indicator means is located on said posterior region of said napkin including a raised profile.

18. The napkin of claim 10 wherein said indicator means is comprised of a dye on the interior of the bodyside covering of said napkin.

19. The napkin of claim 10 wherein said indicator means comprises perforations of the bodyside liner.

20. The napkin of claim 10 wherein said napkin is about 5 to 6 inches in length and said means to indicate accurate placement comprises a teardrop-shaped visual indicator between about ½ inch to 1 inch wide and between about 1¼ and about 2¼ inches long placed to begin between about ½ and about ¾ inch from the posterior end of the said napkin.

21. The napkin of claim 10 wherein said indicator has a width comprising between about 8% and about 20% of the pad length and an indicator length of generally between about 20% and about 40% of the length.

22. A labial pad having an anatomically conformable configuration with a generally ovate geometry defined about a principal longitudinal axis, a minor transverse axis and a generally orthogonal lateral axis, said pad including a laterally upward directed projection lying generally along said longitudinal axis from a prominence proximate the distal end thereof and tapering both forwardly and to the opposed sides along said transverse axis; wherein said projection is configured for disposition within the vestibule of a wearer over a region bounded generally by the posterior labial commissure and the labia majora terminating proximate the latter at a location spaced from the clitoris wherein the area of said projection is provided with an indicator means for connoting the accurate placement of said pad onto said region of the body of the wearer.

23. The labial pad of claim 22, comprising an absorbent body for retention of menses and a fluid transmissive cover overlying at least a portion of the top surface of said pad for passing menses to said absorbent body, wherein said overcover is comprised of a material characterized as physiologically hydrous within the environment of said vestibule.

24. A labial pad comprising a fluid-retentive body bearing a physiologically hydrous cover provided with positioning means for connoting accurate placement of said pad onto the body of the wearer.

25. A labial pad configured for partial interposition within the vestibule of a user to occlude menstrual fluid, comprising a contoured absorbent body defined spatially about a principal longitudinal axis, a minor transverse axis and generally orthogonal lateral axis, having a posterior region for anatomical cooperation within said vestibule and an anterior region for anatomical cooperation over the vulva and spaced from the clitoris of the user; said absorbent body comprised of a plurality of microfibrous webs disposed laterally in face-to-face engagement, lying within said posterior region generally edgewise along said longitudinal axis and within said anterior region generally facewise across said transverse axis wherein said pad is provided with an indicator means for connoting occluding disposition of said pad at least partially within the vestibule of said user.

26. The labial pad of claim 25, including a set along said longitudinal axis for establishing a structural predisposition within said posterior region to form a generally transversely disposed inverted "V"-shaped projection for disposition within said vestibule.

27. The labial pad of claim 26, further comprising a physiologically hydrous cover.

28. The labial pad of claim 26, further comprising a transfer layer of a nonwoven fabric overlying said microfibrous webs.

29. The device of claim 1 comprising a sanitary napkin.

* * * * *